(12) United States Patent
Burbank et al.

(10) Patent No.: US 7,337,674 B2
(45) Date of Patent: Mar. 4, 2008

(54) PRESSURE DETECTOR FOR FLUID CIRCUITS

(75) Inventors: Jeffrey H. Burbank, Boxford, MA (US); James M. Brugger, Newburyport, MA (US); Dennis M. Treu, Bedford, NH (US); Christopher McDowell, Holladay, UT (US)

(73) Assignee: Nx Stage Medical, Inc., Lawrence, MA (US)

( * ) Notice: Subject to any disclaimer, the term of this patent is extended or adjusted under 35 U.S.C. 154(b) by 167 days.

(21) Appl. No.: 11/160,586

(22) Filed: Jun. 29, 2005

(65) Prior Publication Data

US 2007/0000333 A1     Jan. 4, 2007

(51) Int. Cl.
*G01L 7/00*     (2006.01)

(52) U.S. Cl. ....................................................... 73/714

(58) Field of Classification Search .................. 73/714, 73/723, 725, 726, 727, 862.041; 600/562, 600/573, 584; 604/131, 207
See application file for complete search history.

(56) References Cited

U.S. PATENT DOCUMENTS

| | | | |
|---|---|---|---|
| 3,046,788 A * | 7/1962 | Laimins | 73/734 |
| 4,207,551 A * | 6/1980 | Kautzky | 338/4 |
| 4,555,949 A * | 12/1985 | Danby et al. | 73/705 |
| 4,576,181 A | 3/1986 | Wallace et al. | |
| 5,024,099 A | 6/1991 | Jenkins et al. | |
| 5,440,932 A * | 8/1995 | Wareham | 73/730 |
| 5,602,339 A * | 2/1997 | Wareham | 73/730 |
| 5,846,257 A * | 12/1998 | Hood | 606/167 |
| 6,463,813 B1 * | 10/2002 | Gysling | 73/862.59 |
| 6,523,414 B1 | 2/2003 | Malmstrom et al. | |
| 6,579,253 B1 | 6/2003 | Burbank et al. | |
| 6,589,482 B1 | 7/2003 | Treu et al. | |
| 6,638,478 B1 | 10/2003 | Treu et al. | |
| 6,857,326 B2 * | 2/2005 | Specht et al. | 73/862.393 |
| 6,957,588 B1 * | 10/2005 | Kicher et al. | 73/861.52 |
| 7,056,316 B1 * | 6/2006 | Burbank et al. | 604/891.1 |
| 7,121,143 B2 * | 10/2006 | Malmstrom et al. | 73/705 |
| 2004/0060359 A1 * | 4/2004 | Wilson | 73/706 |

* cited by examiner

*Primary Examiner*—Edward Lefkowitz
*Assistant Examiner*—Freddie Kirkland, III
(74) *Attorney, Agent, or Firm*—Miles & Stockbridge, P.C.; Mark A. Catan

(57) ABSTRACT

A pressure measurement device usable for monitoring pressure of fluids such as blood, waste, and replacement fluid in a blood treatment system provides a reliable signal and other benefits by virtue of a number of features of the various embodiments disclosed. The pressure of fluid carried by a vessel or tube is measured by measuring a change in shape of the vessel or tube via a sensor element contacting it. Materials, shape, and mechanical support cooperatively ensure that the little inelastic strain occurs and pressure measurements are repeatable. The embodiments are compatible with the use of disposable vessels and tubes.

10 Claims, 13 Drawing Sheets

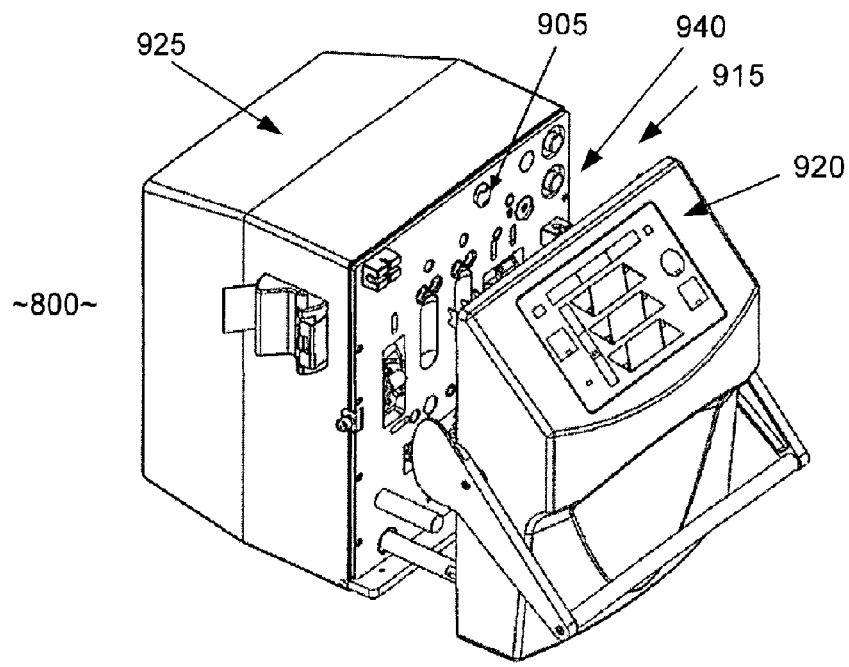
Fig. 17A
Fig. 17B
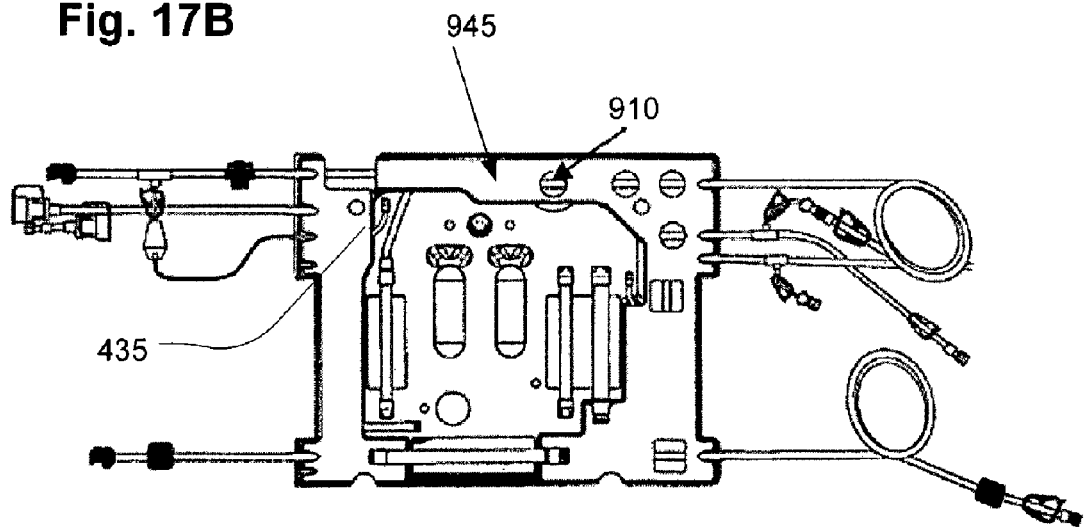

PRESSURE DETECTOR FOR FLUID CIRCUITS

BACKGROUND

Pressure transducers are used widely for pressure measurement. An example prior art device is described in U.S. Pat. No. 4,576,181 and illustrated in FIG. 1A. Such devices require connection to a flow channel or chamber to provide fluid communication with a sensor portion. For example, a flow channel 32 of a prior art device provides fluid communication between a diaphragm 45 and a vessel or conduit 30 containing a fluid whose pressure is to be measured, from some flow or containment system 47. An intermediate fluid in a space 35 on an opposite side of the diaphragm 45 communicates with a pressure transducer 40. The fluid whose pressure is to be measured exerts a pressure on the diaphragm 45 in turn exerting a pressure on the intermediate fluid in space 35. A pressure transducer 40 generates a signal corresponding to the pressure of the intermediate fluid in the space 35 by any of various mechanisms, typically involving a strain gage or load cell.

Another known device for measuring pressure is illustrated in FIG. 1B. In this device, a thin plate 30 has a strain gage 10 on a back surface 31 thereof. A pliant thin-walled vessel 20 rests against a front surface 32 of the thin plate 30. When fluid 25 inside the vessel 20 pressurizes the vessel, which is bounded by walls 15 and 22, thin plate 30 flexes, stretching a strain gauge 10 attached to it, thereby causing a signal from which pressure can be correlated by calibration.

The pressure sensor of FIG. 1B may be employed in medical systems and devices that transport biological fluids. In such systems, the use of certain plastics is very common, due to its durability, flexibility, low cost, and low chemical and biological reactivity. Such plastics, however, when strained, are susceptible to change in terms of their elastic response.

For example, if substantially deformed, thicker walled plastic vessels such as 20 in FIG. 1B will exhibit a condition known as "creep", causing the displacement-versus-pressure response to change over time. Creep is caused by changes in the conformation of polymer molecules over time. Creep may lead to errors in measurement of pressure changes in a configuration such as that of FIG. 1B.

Referring to FIG. 1C, another type of prior art pressure sensor in which a pressure transducer 50 is in pressure communication with an interior 70 of a drip chamber 60. Blood flows through an inlet tube 65 and out an outlet tube 75 while a trapped volume of air 62 communications pressure to the pressure transducer 50 through a coupling tube 57. An isolator 55 protects the pressure transducer 50 by preventing any flow through it via a flexible membrane within it (not shown).

BRIEF DESCRIPTION OF THE DRAWINGS

FIG. 17A is a diagonal view of a blood treatment machine suitable for use with the cartridge of FIG. 17A.

FIG. 17B is an illustration of a cartridge and tubing set which is suitable for use in a blood treatment machine.

DETAILED DESCRIPTION OF THE EMBODIMENTS

Figure 1A:
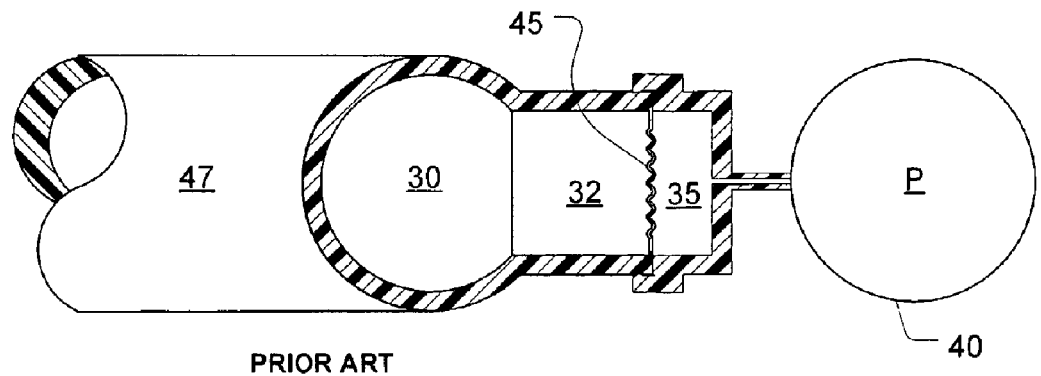
FIG. 1A is one type of pressure sensor according to the prior art.
Figure 1B:
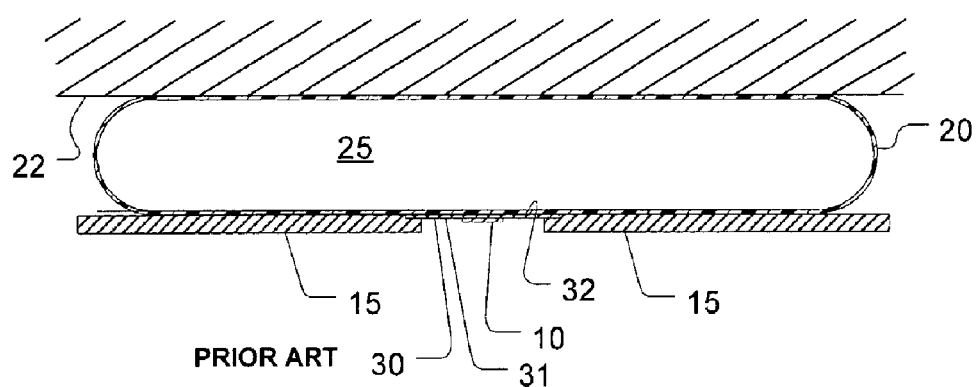
FIG. 1B is another type of pressure sensor according to the prior art.
Figure 1C:
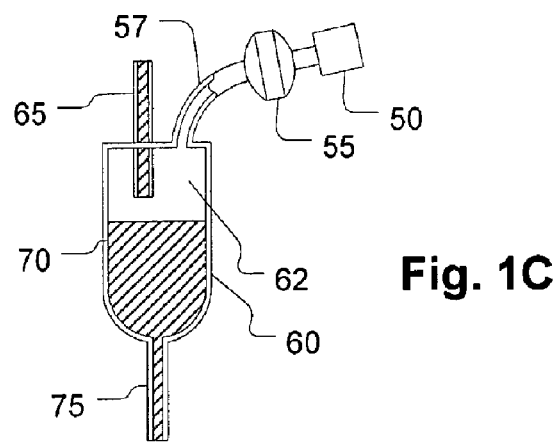
FIG. 1C is yet another type of pressure sensor according to the prior art.
Figures 2A, 2B:
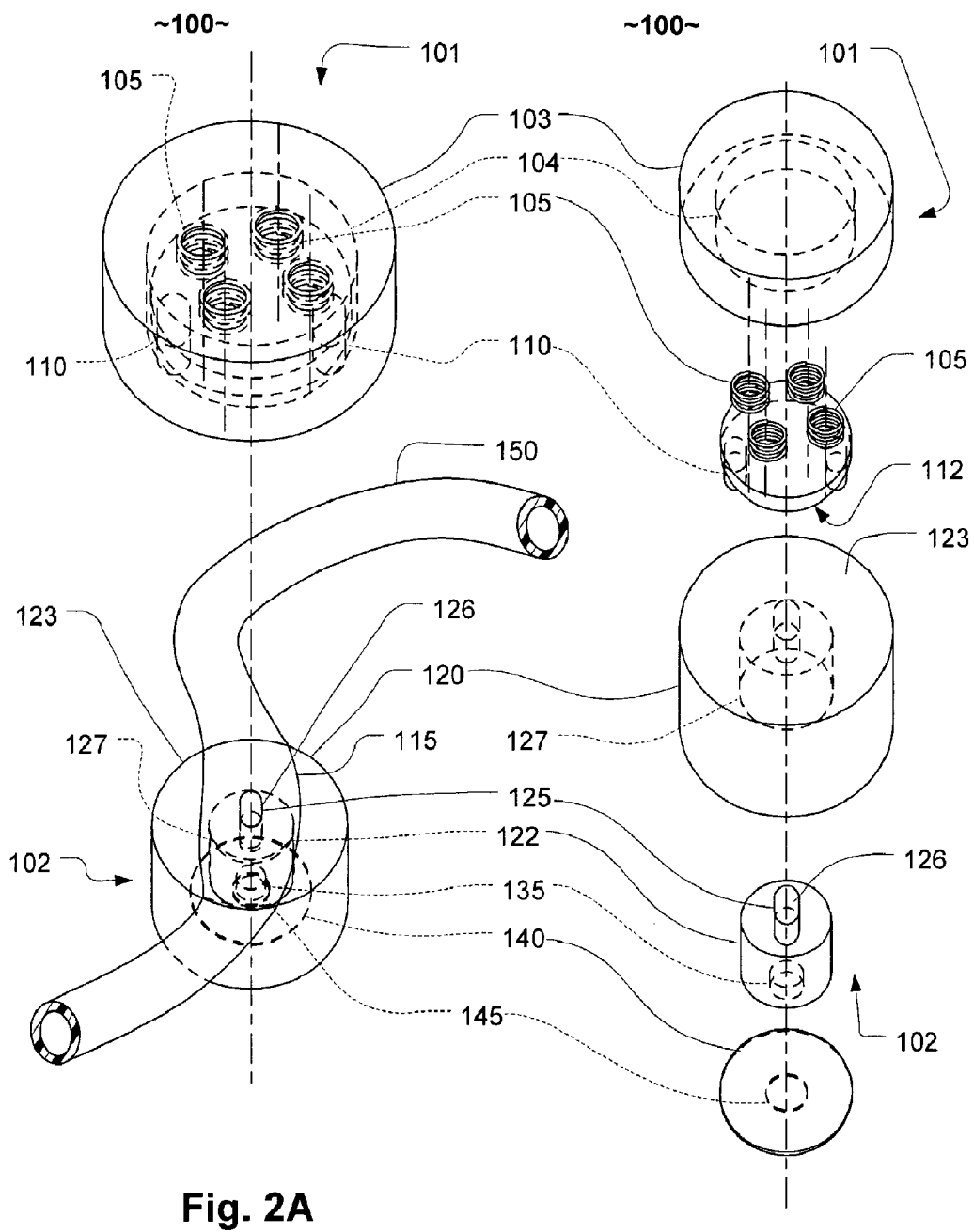
FIG. 2A is a diagonal projection of two opposing portions of an inventive pressure transducer that detects changes in the shape of a flattened portion of a tube to measure pressure inside the tube.
FIG. 2B is an exploded view of the components of the transducer of FIG. 2A.
Figure 3A:
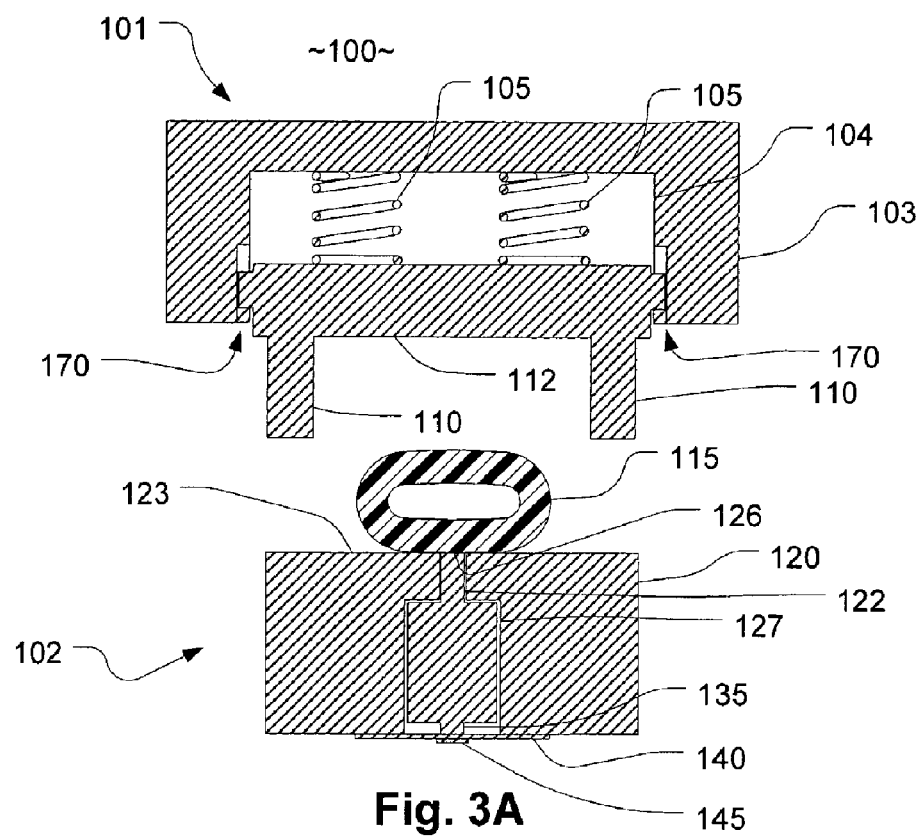
FIG. 3A is a cross-sectional view of the transducer of FIGS. 2A and 2B, showing the opposing parts separated prior to clamping around a portion of a plastic tube.
Figure 3B:
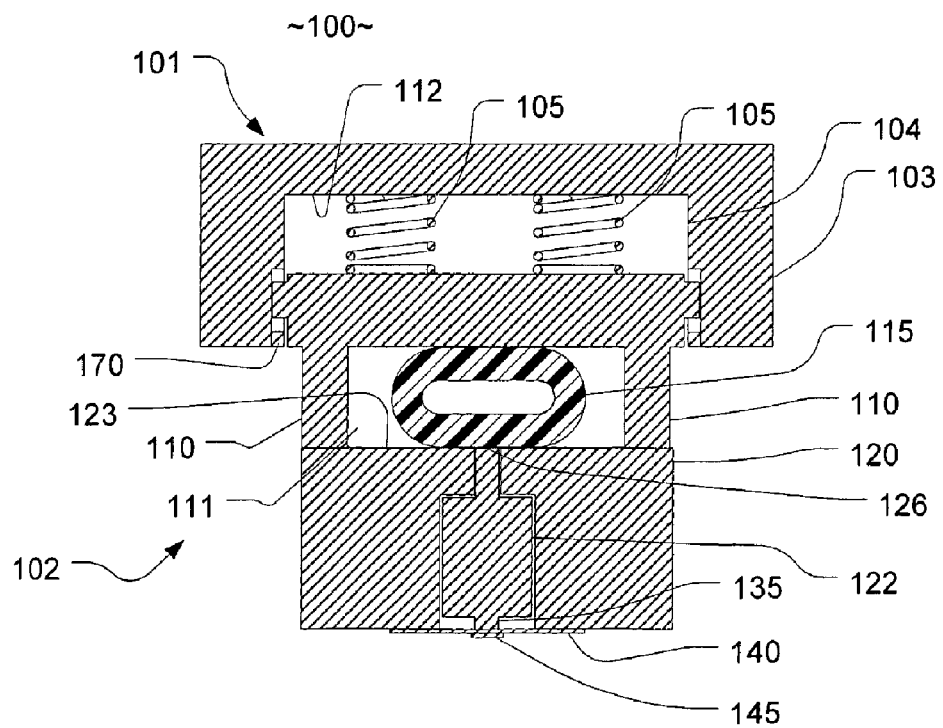
FIG. 3B is a cross-sectional view of the transducer of FIG. 3A, showing the opposing parts in a clamped position suitable for measurement of pressure changes in the plastic tube.

Referring now to FIGS. 2A, 2B, 3A, and 3B, a pressure sensor 100 includes backing portion 101 that holds a flattened portion 115 of a tube 150 against a sensor portion 102 when the pressure sensor 100 is in a closed operational configuration as shown in FIG. 3B. The backing portion 101 has springs 105 in a cavity 104 to urge a backing plate 112 against the flattened portion 115 of the tube 150. Standoffs 110 provide repeatable spacing in a receiving gap 111 that is defined when the pressure sensor 100 is in the closed operational configuration. A surface of the tube 150 flattened portion 115 is held against a tip 126 of an anvil 122 held slidably within a guide 127. A backing retainer 103 limits a range-of displacement of the backing plate 112 by means of a guide/catch mechanism 170, which may permit vertical movement of the backing plate 112 relative to the backing retainer 103.

When the backing portion 101 is brought together with the sensor portion 102, the standoffs 110 rest against a housing stage 120 as shown in FIG. 3B. The springs 150 are compressed such that the receiving gap 111 is reliably defined. The tube 150 flattened portion 115 is shaped such that it is only minimally compressed in the receiving gap 111. This helps to ensure that while the flattened portion 115 rests in the receiving gap 111 it is minimally strained. In addition the flattened portion 115 of the tube 150 is supported by the top 123 of the housing stage 120 so that when pressure increase in the flattened portion 115 of the tube 150, there is minimal strain of material of which the tube 150 is made. The benefit of this is that in configurations in which the material, of which the tube 150 is made, is prone to creep, little change in the shape and elastic response of the material may occur due to the flattened portion 115 being held in the receiving gap 111 and pressurized. These features translate to a reduced susceptibility of the apparatus to respond variably over time to pressure in the tube 150 due to the creep, to a smoother monotonic relationship between pressure and strain.

When fluid in the tube 150 is pressurized, the flattened portion 115 presses against the tip 126 of the anvil 122 forcing the anvil 122 toward a flexible plate 140 with an attached strain gage 145. A pin 135 presses against the flexible plate 140 when the anvil 122 is forced toward it by pressure in the tube 150. The amount of strain to which the strain gage 145 is subjected (due to pressure inside the tube 150 and transmitted through the flattened region 115) can be altered by changing the shape and or size of the pin 135, due to the differences in the bending moment to which the flexible plate 140 is subjected by displacement of the anvil 122. The pressure may be measured by means of a curve fitted to a pressure-versus-strain gage signal curve generated by means of a calibration procedure. Calibration is discussed further below.

The tip 126 of the anvil 122 and the top 123 of the housing stage 120 may form a nearly continuous flat surface, with the top 126 jutting only slightly above the top 123 of the housing stage 120. In this way, the deformation of the flattened portion 115 of the tube 150 may be minimal. This may be a benefit where the material of the tube 150 is subject to creep. Also, the overall configuration may be such that the displacement of the anvil 122 may have a low magnitude to help reduce the potential creep problem.

Figure 4A:
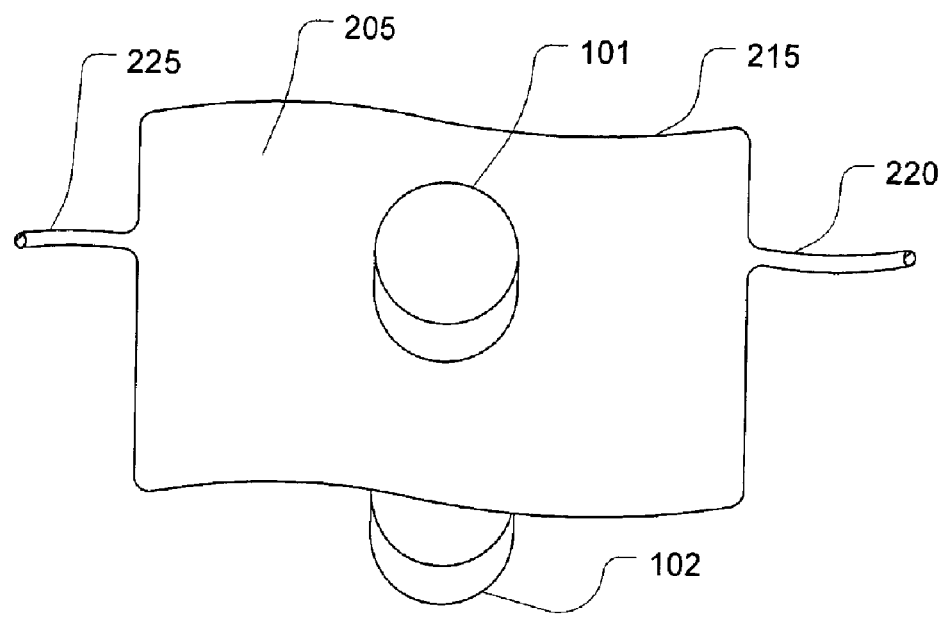
FIG. 4A is a diagonal projection of the opposing halves of a pressure transducer suitable for measuring pressure changes in a thin-walled flexible vessel or conduit having large dimensions such that a confining spacing is provided by some external mechanism.
Figure 4B:
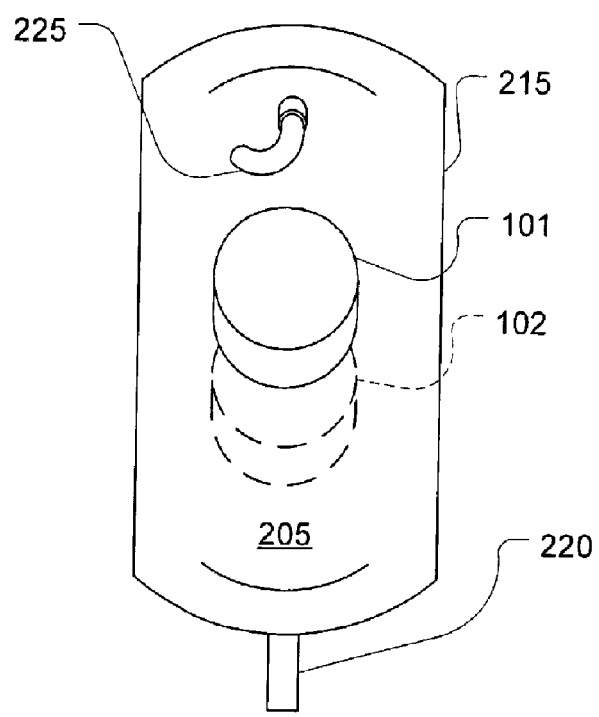
FIG. 4B is a diagonal projection of the opposing halves of a pressure transducer suitable for measuring pressure changes in a hanging fluid bag commonly used for biological fluids and having large dimensions such that a confining spacing is provided by some external mechanism.

Referring now also to FIGS. 4A and 4B, the pressure sensor 100 may be used detect pressure in a variety of vessels other than a tube 150. For example, a flexible chamber 215 connected to, or connectable to, a flow conduit (not shown) by flow lines 225 and 220, may have very flexible walls 205 reducing the magnitude of the potential creep problem. Backing 101 and sensor 102 portions without standoffs 110 may be brought into a desired relationship by a suitable structure such that when pressure is applied to fluid in the flexible chamber 215, the anvil 122 is forced toward the flexible plate 140 thereby permitting measurement of pressure by means of the strain indicated by the strain gage 145. Although not shown, portions of the flexible chamber 215 outside that subtended by the backing 101 and sensor 102 portions of the pressure sensor 100 may be confined in a recess defined by walls of a machine (e. g., a renal therapy machine as described in U.S. Pat. Ser. Nos. 09/513,564, 09/512,927, and 09/513,773 hereby incorporated by reference in their entirety as fully set forth herein). Such walls may be substantially coplanar with the backing plate 112 and the top 123 of the housing stage 120. Pressure may also be measured in a fixed vessel such as shown at 235, which defines, flow-wise, a dead-end.

A number of configurations are preferred for use with the pressure sensor 100 as well as others discussed in the instant specification. The preferred configuration may depend on various features, including the material from which the tube or vessel is made, the thickness of the tube or vessel wall relative to the top of the anvil 126, the shape of the wall, the length of time during which the tube or vessel is subjected to pressure, the amount of pressure to which the tube or vessel is subjected, the conformity of the surface defined by the top of the anvil 126 and the top 123 of the housing stage 120. FIGS. 5A through 5C and 6A through 6F illustrate vessels or tubes of a variety of configurations for purposes of illustrating various features that may influence the design of a pressure sensor according to the embodiments disclosed and variations thereof.

Figure 5A:
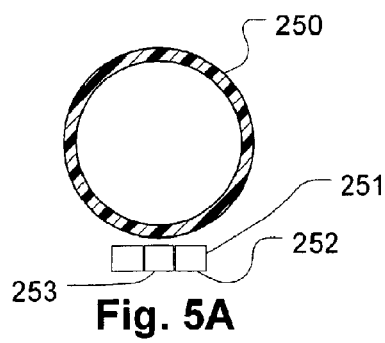
FIGS. 5A and 5B are cross-sectional views of circular and elliptical tubes or vessels for purposes of discussing the effect of hoop-strength on pressure measurement.
Figure 5B:
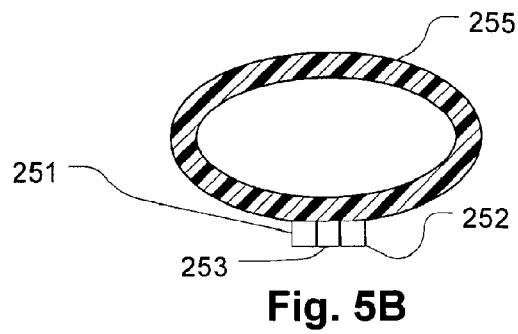
Figure 5C:
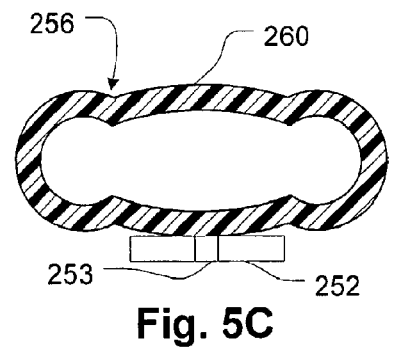
FIG. 5C is a cross-sectional view of a tube or vessel for purposes of discussing the effect of features that increase material strain and thereby impact pressure measurement.

In FIG. 5A, a vessel or tube 250 with a substantially circular cross-section has significant hoop strength requiring a great deal of material strain to displace a contact sensor such as the anvil 122 described with reference to the foregoing figures. The same is true for a tube or vessel 255 having an elliptical shape (FIG. 5B), and for plastic tubing 260 of a generally oval shape with rigidity-enhancing ridges 256 as shown in FIG. 5C. In addition, the thickness of the walls affects the degree of strain to which the material of the tube or vessel must be subjected to generate a displacement for actuating the foregoing embodiments and others described elsewhere in the instant specification. Note that the tubes or vessels 250, 255, and 260 shown above are illustrated in a relaxed state. To be used in a pressure sensor device as described in the current specification, the tubes or vessels 250, 255, and 260 may be compressed to force an outer surface against the tip 253 of an anvil and housing stage surface 252 to preload the tube or vessel 250, 255, and 260 or not. In either case, whether the tube or vessel 250, 255, and 260 is preloaded or not loaded in advance of calibration and pressure sensing, the creep may play a significant role in the deformation of the tube or vessel 250, 255, and 260. When preloaded, the tube or vessel 250, 255, and 260 may gradually deform thereby generating a lower elastic rebound over time making the pressure signal from calibration less related to the pressure signal after calibration. If not preloaded, the variation of shape due to pressure change would tend to cause the same effect, namely, a time-varying response due to gradual accommodation to a current shape.

The above problems relating to creep may be overcome by suitable choice of materials. For example, a material which is not subject to creep may be used. Alternatively, or in combination with such a material selection, the wall thickness of any of the foregoing shapes or similar may be reduced. For example, see FIGS. 6C-6E. FIGS. 6C and 6D show the circular cross-section shapes of FIG. 5A with thinner walls that the embodiment of FIG. 5A. FIGS. 6D and 6E show the elliptical and complex cross-section shapes of FIGS. 5B and 5C with thinner walls. FIG. 6C illustrates preloading of the circular cross-section tube or vessel 250A by compressing the latter between a backing surface 254 and an anvil 253 and stage 252 combination forming an opposing surface. If the tube or vessel 250A has substantial strength and elasticity, negative gage pressures may be measured and preloading may be used to select the response characteristic.

In contrast, by providing a tube (or vessel) having a flattened portion that contacts the pressure sensor (see FIGS. 6A through 6F, described in more detail below), the contact area for the pressure sensor is increased. In addition, by using a relatively thin-walled and/or flattened portion of a tube or vessel, preload strain becomes less of a problem and any pressure changes within the it are transmitted more quickly and reliably to the pressure sensor.

Figure 6A:
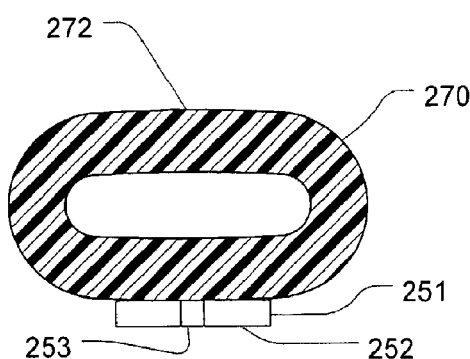
FIG. 6A is a cross-sectional view of an example of a tube or vessel configuration for purposes of discussing features that ameliorate pressure measurement even for thick material.
Figure 6B:
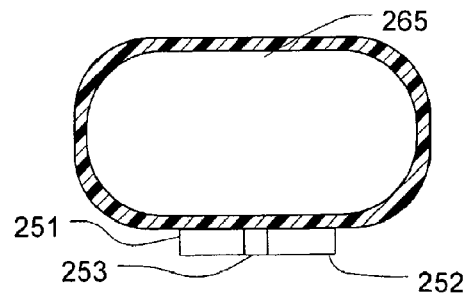
FIGS. 6B-6E are cross-sectional views of tubes or vessels for discussing the effect of using thin walls and other features to ameliorate creep effects.
Figure 6C:
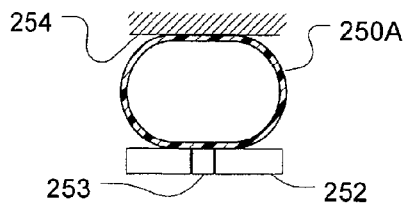
Figure 6D:
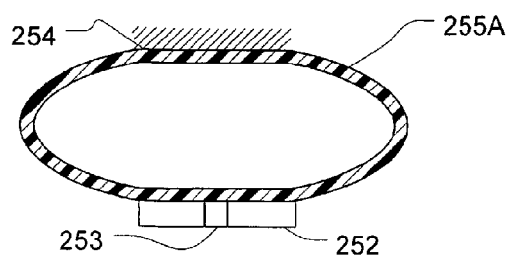
Figure 6E:
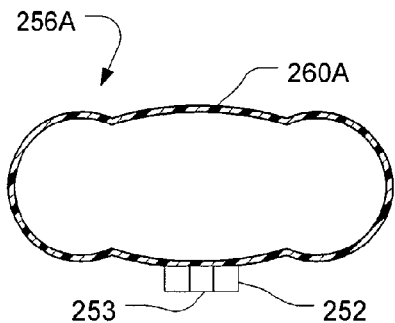
Figure 6F:
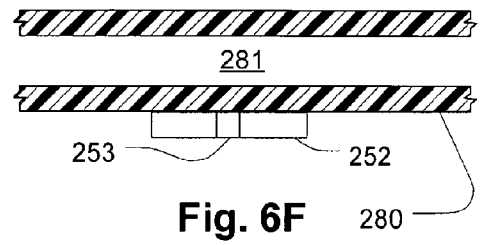
FIG. 6F is a cross-sectional view of a tube or vessel for discussing the effect of aspect ratio and other features to ameliorate creep effects.

In one aspect, a thick-walled tube 270 having a flattened portion 272 provides an enhanced area that contacts not only the central portion 253 of pressure sensor 251, but also the outer portions 252 as well (FIG. 6A). In a second aspect, illustrated in FIG. 6B, a thin-walled tube 265 having the same conformation as that of FIG. 6A not only provides the enhanced contact area for pressure sensor 253, but also further produces little strain, resulting in a greatly reduced amount of creep. In another aspect, a thin walled circular tube 250A illustrated in FIG. 6C, is flattened between backing surface 254 and pressure sensor 251 causing the thin-walled circular tube 250A to form a more oval shape. Similarly, in another embodiment, a thin walled elliptical tube 255A illustrated in FIG. 6D, is flattened by backing surface 254 and the pressure sensor 251. In yet another aspect, shown in FIG. 6E, the strain at the site of contact of pressure sensor 251 may be reduced even in the presence of rigidity-enhancing ridges 256A. In another aspect, a portion of a circular or elliptical piece of tubing may be flattened at the point of contact with pressure sensor 253 to provide the enhanced contact area. The flattened portion may be created by physical alteration of the tubing, or by incorporation of a different piece of tubing that is flatter than the rest of the tubing. One method of creating the flattened portion of a tube, such as the flattened portion 272 of the tube 270 shown in FIG. 6A is to thermoform a cylindrical tube by heating and compressing it. In another aspect, the flattened portion may also be thinner than the rest of the tubing. Referring to FIG. 6F, the walls 280 of a non-tubular vessel enclosing a volume 281 with a pressure inside can be sensed by means of a pressure sensor 251 in a manner similar to the foregoing embodiments.

Figure 7:
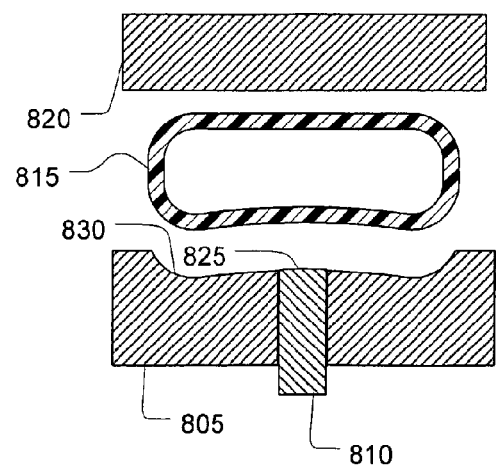
FIG. 7 is a cross-sectional view of a pressure transducer according to another aspect of the present invention, in which the transducer is shaped so as match a tube or vessel having a non-flat-shaped portion.

In another aspect, as shown in FIG. 7, creep in a flattened portion of a tube 815 may be reduced by arranging the tube in a housing so that the tubing adopts a concave shape where the tubing rests on top of the anvil 810. Tubing 815 is held in place atop anvil 810 between backing retainer 820 and housing stage 805 in a formed inner face 830, and contact anvil 810 at anvil tip 825. The formed inner face 830 may have other shapes and may be convex, saddle-shaped, or asymmetrical or three dimensional curves in them.

Other methods and devices may be used in place of the anvil shown in FIGS. 3A-3B to transmit detected pressure changes to a measuring device. As an example, a cantilever mechanism may be used to transmit pressure changes to a pressure transducer.

Figure 8:
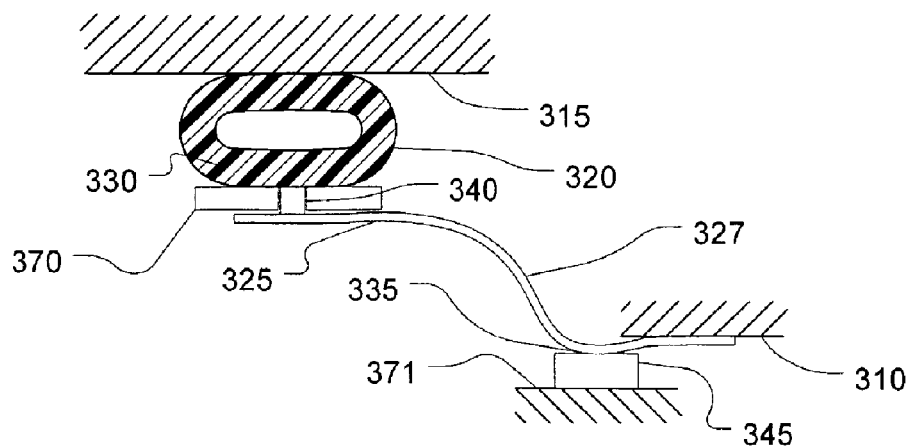
FIG. 8 is a cross-sectional view of a pressure transducer that uses a cantilever to transmit pressure changes to a load sensor.

Referring now to FIG. 8, a flattened portion 330 of a tube 320 is held in place between a wall 315 and a fixed base 370. An anvil 340 contacts flattened portion 330. The distal end of anvil 340 is affixed to an arm 327 of cantilever 325. At the other end of cantilever 325 is a knee 335 in contact with a pressure transducer 345 mounted on a fixed base 371. Cantilever 325 terminates at and is fixed to a fixed base 310. Movement of anvil 340 is translated through cantilever arm 327 and is sensed by pressure transducer 345.

Figures 9A, 9B:
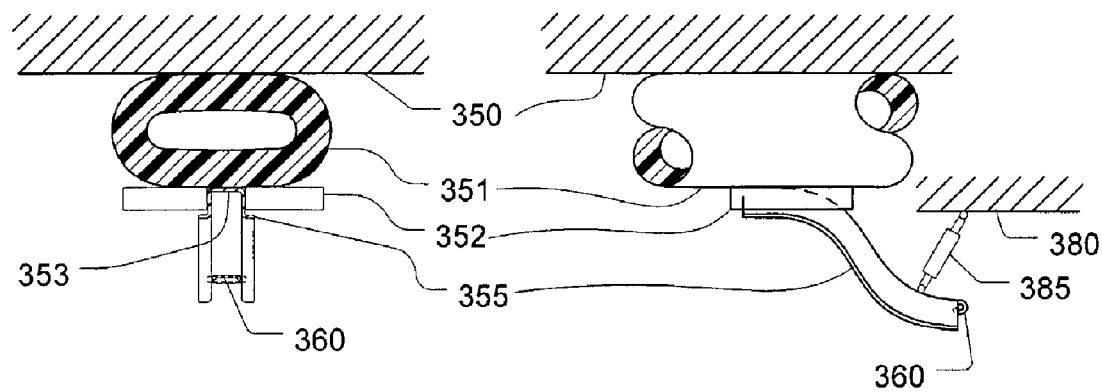
FIG. 9A is a cross-sectional view of a pressure transducer that uses a cantilever to transmit pressure changes to a tension transducer or extension displacement transducer.
FIG. 9B is a side view of the pressure transducer design of FIG. 9A.

Referring now to FIGS. 9A and 9B, in the alternative embodiment, pressure changes may be transmitted to an extendible type pressure transducer such as a displacement-type strain gage 385. An arm 355 pivots from a fixed hinge 360. An end portion 353 of the arm 355 is in contact with a tube 351 such that pressure changes within the tube 351 cause the arm 355 to move.

The arm 355 movements are transmitted to a displacement-type strain gage 385 connected between the arm 355 and a fixed base 380. The end portion 353 of the arm 355 is surrounded by a fixed base 352 which supports the tube 351.

Figure 10:
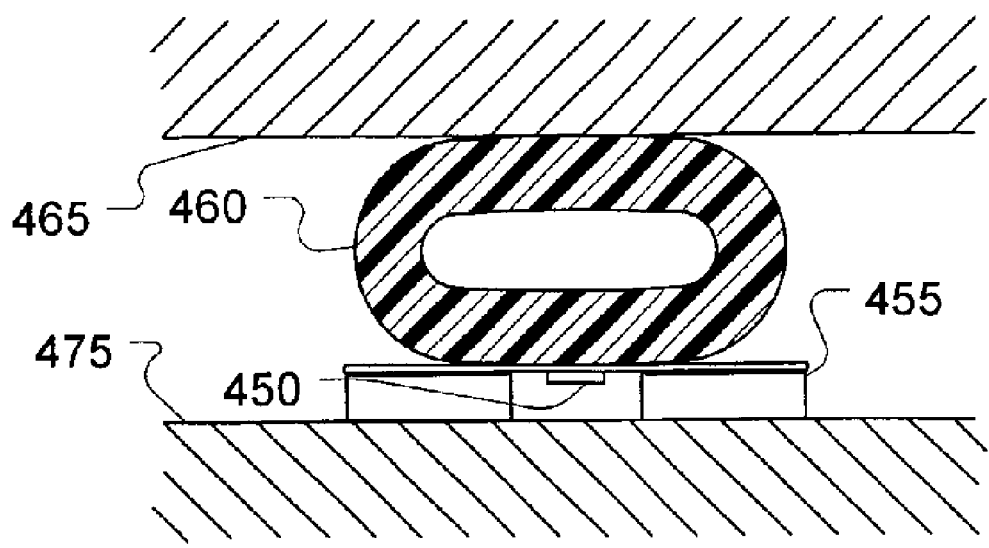
FIG. 10 is a cross-sectional view of a pressure transducer providing a direct contact between a metal plate bearing a strain gage and a flattened portion of a tube or vessel.

In another aspect of the present invention, the flattened portion of tubing may directly contact a strain gauge and flexible plate. In other words, the device functions without an anvil, cantilever, etc., to transmit the detected pressure changes to a pressure transducer. Referring to FIG. 10, flattened portion 460 is held in place between a wall 465 and flexible plate 455 atop a strain gage 450 mounted on a fixed base 475. Movement in flexible plate 455 is transmitted directly to strain gage 450.

Figure 11:
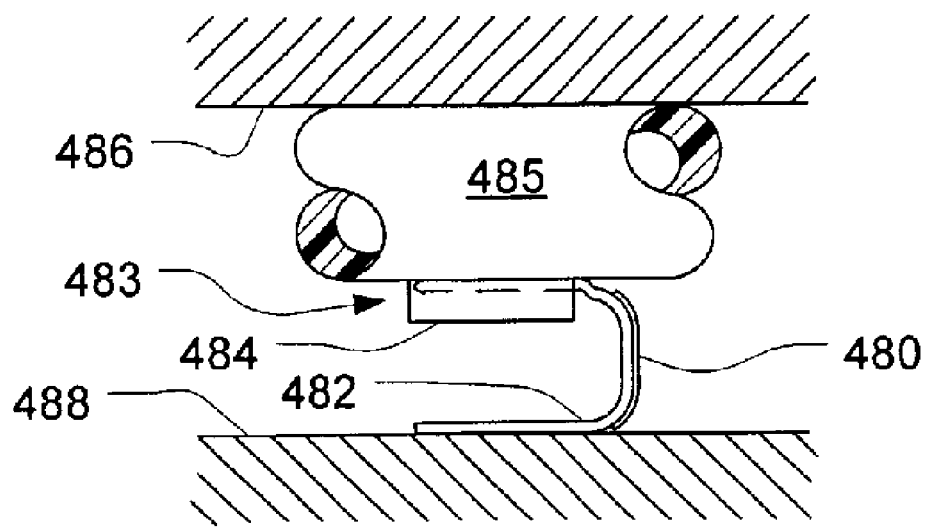
FIG. 11 is a side view of a curved strain gage mounted on a flexible pillar transducer.

In another aspect of the invention, the pressure change is sensed by a curved strain gauge mounted on a flexible pillar transducer, as shown in FIG. 11. Tubing flattened portion 485 is mounted between a wall 486 and a flat terminus 483 of a flexible pillar transducer 482. Flexible pillar transducer 482 is held in contact with tubing flattened portion 485 by the flexible pillar, which urges the terminus 483 against the tubing flat portion 485. The other end of flexible pillar transducer 482 is attached to a fixed base 488. Attached to the outside surface of flexible pillar transducer 482, between the arm attached to pressure sensor 484 and the arm attached to wall 488, is a strain gauge 480. Pressure changes in tubing flattened portion 485 produce a change in the shape of flexible pillar transducer 482, which is detectable by the strain gauge 480.

In the embodiment illustrated in FIG. 3B, anvil 122 may be subject to frictional resistance to movement within housing stage 120. Such resistance to movement may result in loss of sensitivity or an apparent "spike" in pressure as the anvil suddenly overcomes the resistance. In another aspect of the present invention, the device may be constructed to reduce frictional contact between anvil 122 and housing stage 120.

Figure 12:
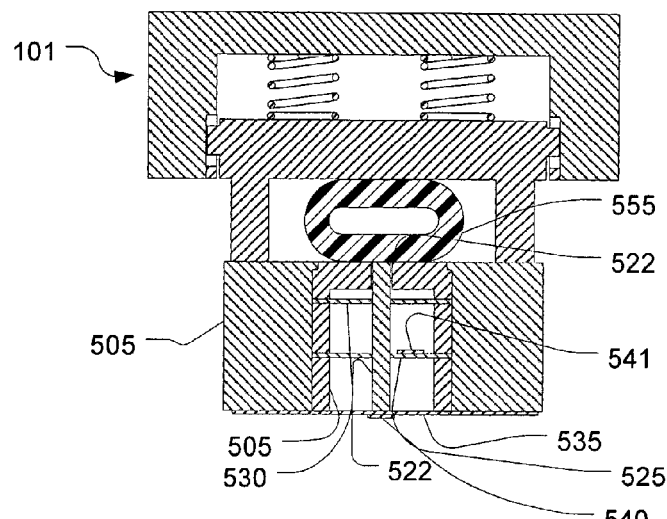
FIG. 12 is a cross-sectional view of an alternative mounting mechanism for the anvil employed in the embodiment of FIGS. 2A and 2B and an alternative location for a strain gage.

Referring now to FIG. 12, anvil 522 is held within housing stage 505 with one or more rings 530. Although in FIG. 12 a total of two internal rings are shown, it is intended that any number of rings 530 could be employed consistent with the goal of reducing frictional contact with anvil 522 while maintaining anvil 522 in a fixed position at rest. As in FIG. 3B, when fluid in the tube 555 is pressurized, the flattened portion presses against the anvil 522, forcing plunger 520 toward a flexible plate 535 with attached strain gauge 540. Alternatively or in combination, one or more strain gages 541 may be mounted on rings 525 to detect pressurization of tube 555.

In another aspect, the pressure transducer is in the form of a strain gage mounted on a flexible plate that contacts the flattened portion of a tube 555 mounted on a wall 565.

Figure 13A:
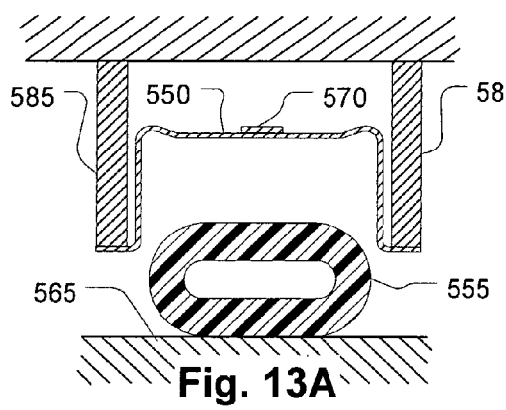
FIG. 13A is a cross-sectional view of a pressure transducer, in which a flexible plate with a strain gage is positioned against a cross-sectional view of a pressure transducer. The pressure transducer is shown in an open position.
Figure 13C:
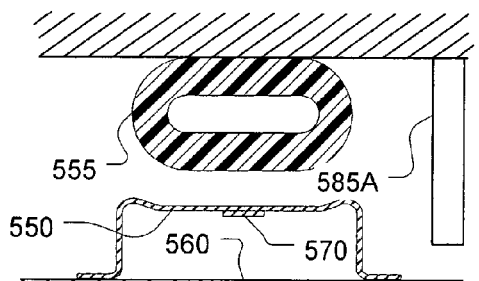
FIG. 13C is another aspect of the pressure transducer of FIG. 13A, in which the pressure transducer is mounted on the base wall. The pressure transducer is shown in an open position.
Figure 13B:
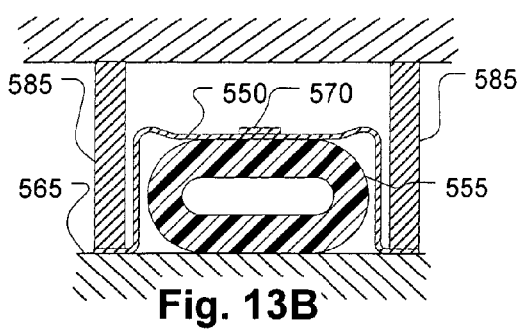
FIG. 13B is a cross-sectional view of the pressure transducer of FIG. 13A, shown in a closed operating position that enables measurement of pressure changes within the flattened portion.
Figure 13D:
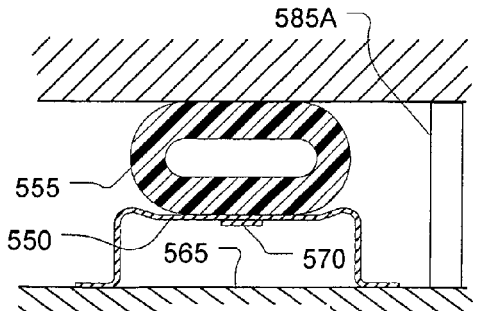
FIG. 13D is a cross-sectional view of the pressure transducer of FIG. 13C, shown in a closed operating position that enables measurement of pressure changes within the flattened portion.

Referring now to FIGS. 13A and 13B, a flexible plate 550 is mounted between one or more standoffs 585. A strain gauge 570 is mounted on flexible plate 550, at a position where flexible plate 550 contacts the flattened portion of tube 555 when standoffs 585 are lowered to contact wall 565, as shown in FIG. 13B. Another aspect of the invention is shown in FIGS. 13C and 13D, in which tube 555 is mounted between standoffs 585, and a flexible plate 550 is mounted on wall 565. A strain gage 570 is mounted on flexible plate 550, and contacts the flattened portion of tube 555 when tube 555 is lowered so that standoff 585 contacts wall 565.

Although FIGS. 13A and 13B show two standoffs in opposing position, and FIGS. 13C and 13D show a single standoff, it is intended that the present invention not be limited to these embodiments. For example, more than two standoffs may be used, and they may be regularly or irregularly spaced. In addition, although strain gauge 570 is shown in FIGS. 13A through 13D as being located in the center of flexible plate 550, it may be mounted at any point along flexible plate 550 where flexible plate 550 contacts the flattened portion of tube 555.

Figure 14A:
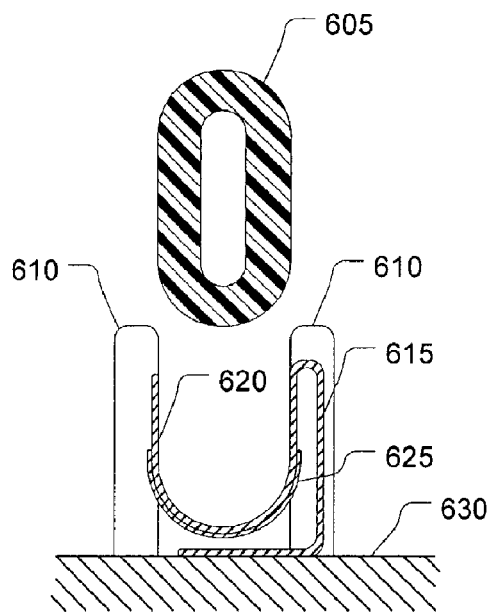
FIG. 14A is a cross-sectional view of a pressure transducer, in which a flexible plate with a curved strain gage is positioned to wrap partly around a tube or vessel. The pressure transducer is shown in an open position.
Figure 14B:
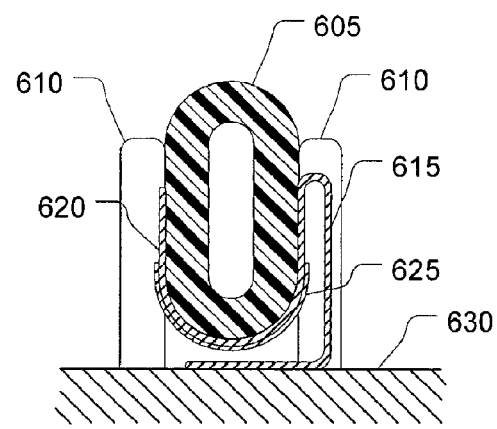
FIG. 14B is a cross-sectional view of the pressure transducer of FIG. 14A, shown in a closed operating position that enables measurement of pressure changes within tube or vessel.

FIGS. 14A and 14B illustrate yet another aspect of the present invention, in which a transducer having a flexible plate and bearing a curved strain gauge is positioned to wrap partly around a tube or vessel. As shown in FIGS. 14A and 14B, flexible plate 620 is mounted between a pair of opposing side supports 610, such that it forms a curved shape between side supports 610. Flexible plate 620 may be mounted on a wall 630, as shown. The curved shape of flexible plate 620 matches the outside curve of a tube 605. A curved strain gauge 625 is mounted on flexible plate 620, such that tube 605 may fit inside and in contact with flexible plate 620. Strain gauge 625 is located on the outside portion of flexible plate 620.

Calibration of the pressure sensor may be achieved by a standard curve-fitting procedure using a calibration system.

Figure 15:
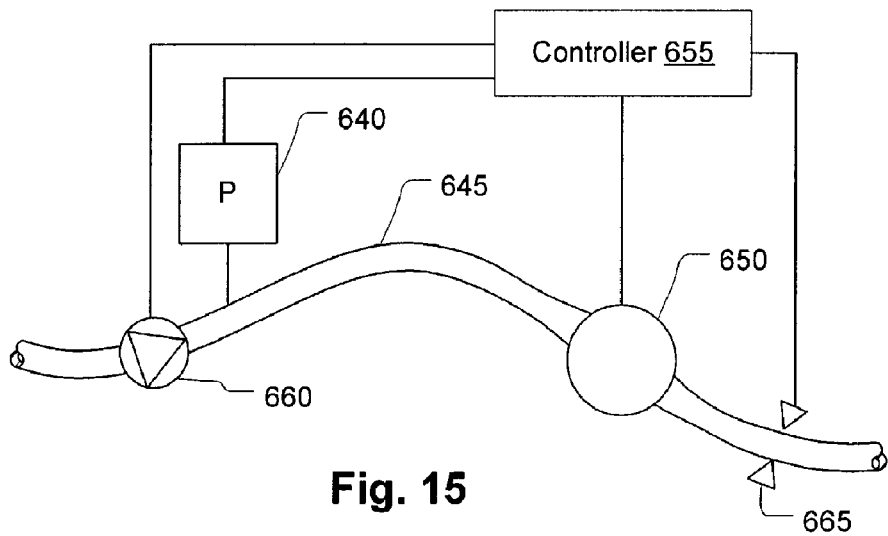
FIG. 15 illustrates an automatic calibration configuration for use with various aspects of the present invention.

Referring to FIG. 15, a calibration system includes a pump 660 connected via a tube 645 to a pressure sensor 650. The rate of fluid flow through the tubing 645 and the pressure sensor 650 is controlled by either or both of the pump 660 or a clamp 665 downstream from the pressure sensor 650. The pump 660 and the clamp 665 are controlled by a controller 655. A precalibrated pressure sensor 640 is located in the tubing line between the pump 660 and the clamp 665. To calibrate pressure sensor 650, the controller 655 establishes a predetermined internal pressure from precalibrated pressure sensor 640 by altering the flow rate of pump 660 or the degree of closure of clamp 665, or both. The controller 655 then measures the output from pressure sensor 650, and associates the output with the predetermined pressure.

The process is performed for at least two different pressure settings, and the results are used to establish a calibration curve for the pressure sensor 650 (i. e., output of pressure sensor 650 vs. pressure).

A number of configurations are preferred for use with the pressure sensor as well as others discussed in the instant specification. The preferred configuration may depend on various features, including the material from which the tube or vessel is made, the thickness of the tube or vessel wall relative to the top of the anvil, the shape of the wall, the length of time during which the tube or vessel is subjected to pressure, the amount of pressure to which the tube or vessel is subjected, the conformity of the surface defined by the top of the anvil and the top of the housing stage.

Figure 16:
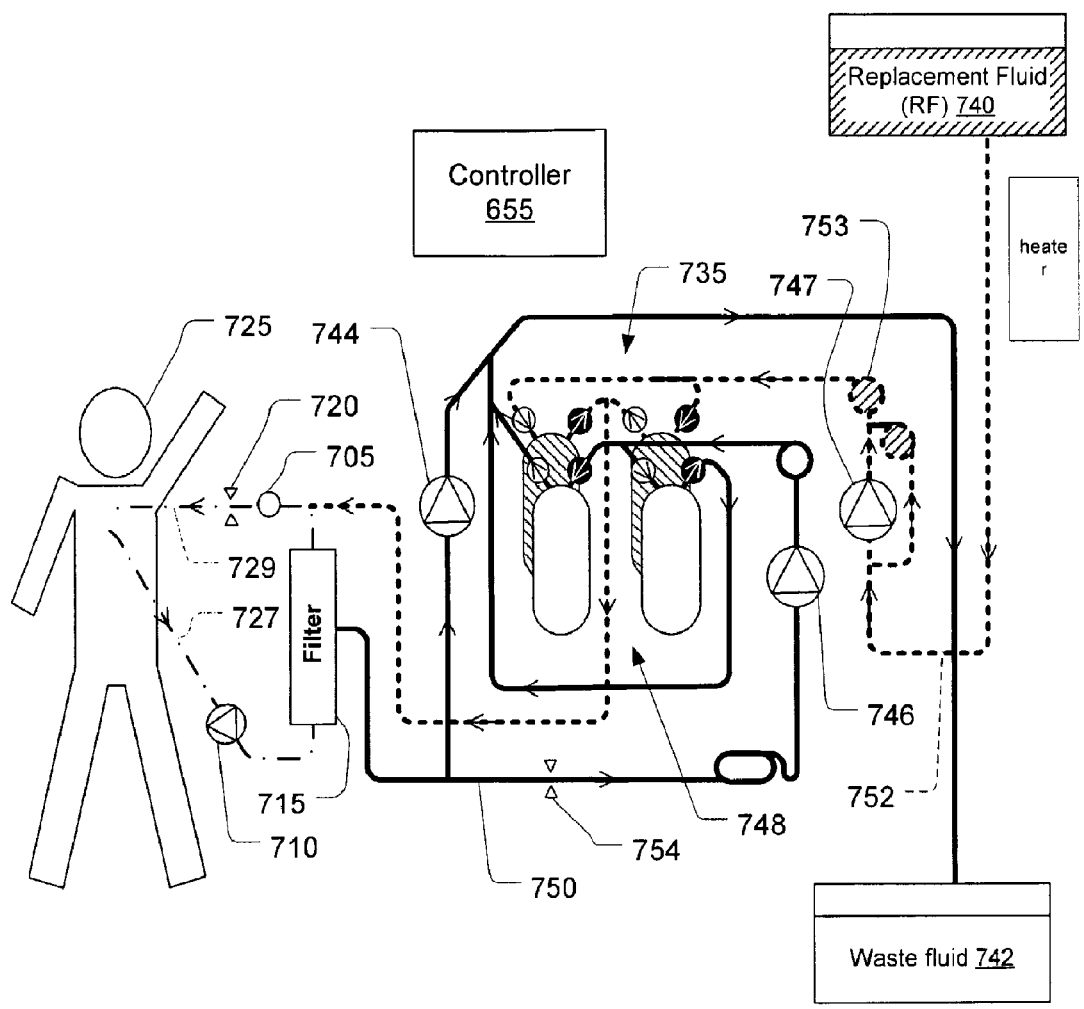
FIG. 16 is a schematic diagram of a blood-processing machine, which may incorporate one or more of the various aspects of the present invention.

The use of the pressure sensor of the present invention in a blood treatment machine is illustrated schematically in FIG. 16. The operation of the blood treatment machine is described in detail in copending U.S. patent application Ser. No. 09/513,911, filed Feb. 25, 2000, hereby incorporated by reference in its entirety. Controller 655 regulates the flow rate of pumps 710, 744,746, and 747 to flow blood from the patient, through a hemofilter 715, and then back to the patient. The machine includes a blood handling unit, a fluid management unit, and a ultrafiltration unit. The blood-handling unit circulates the patient's blood in a controlled manner through the hemofilter 715 and back to the patient after treatment. Note that the hemofilter 715 may be a dialyzer as well. The hemofilter 715 removes waste fluid, containing urea and other toxins, from the blood. The fluid management unit replaces the waste fluid with a sterile replacement fluid for return with the treated blood to the patient's blood supply. The replacement fluid also acts to maintain the patient's electrolytic balance and acid/base balance. The ultrafiltration unit removes waste fluid from the patient without the need for addition of replacement fluid.

Referring now to FIG. 16, blood from the patient 725 is pumped by pump 710 through hemofilter 715 via arterial blood supply line 727, and then returned to the patient 725 via venous return line 729. Wastes, including liquid and uremic toxins, are separated by the hemofilter 715 from the rest of the blood.

The waste material exits the hemofilter 715 and is separated into an ultrafiltration path and a balancing path. Waste material in the ultrafiltration path is moved by pump 744 to a waste fluid container 742. Waste material in the balancing path is pumped by pump 746 through an inline balancing mechanism 749 that displaces replacement fluid, pumped by another pump 747, drawn from a replacement fluid chamber 740. Various valves, pumps and sensors are employed to determine and deliver the appropriate amount of replacement fluid required to insert into the venous return line to maintain the patient's blood pressure.

The pressure sensor 705 of the present invention is placed in the venous return line to measure venous pressure in the patient's return blood line.

Figure 17C:
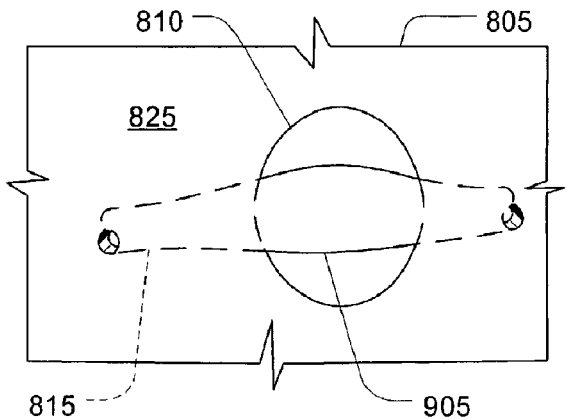
FIG. 17C is an illustration of a pressure transducer suitable for use in the cartridge of FIG. 17B, as mounted in the blood treatment machine of FIG. 17A.

FIG. 17A illustrates a blood treatment machine 800 that may incorporate the pressure sensor of the present invention. FIG. 17B illustrates a cartridge 805 that is insertable in a space 915 in the blood treatment machine 900. The blood treatment machine 800 has a first portion 920 that closes in a clamshell fashion onto a second portion 925 causing various actuators and sensors 940 to engage tubing and other components 945 held by the cartridge 805. Among these components is a sensor, a portion of which is visible at 905, which contacts a flattened tube portion 910 supported by the cartridge 805. The cartridge 805 may be disposable. FIG. 17C shows an enlarged view of the flattened tube portion 910, which may be in a venous return line of the cartridge of FIG. 17A.

Referring now to FIG. 17C, a portion of the cartridge 805 supports a tube 815 with the flattened tube portion 910 that engages the sensor partly visible at 905. Note that in an alternative embodiment, the portion 910 may be cylindrical rather than flattened as indicated or its flattened dimension may be oriented differently depending on the configuration of the sensor with which it is configured to mate. An opening 810 may be provided to give the sensor (partly shown at 905) access to the portion flattened portion 910. The cartridge may or may not have a panel 825, that is, it may be an open support structure (not illustrated).

Figure 18:
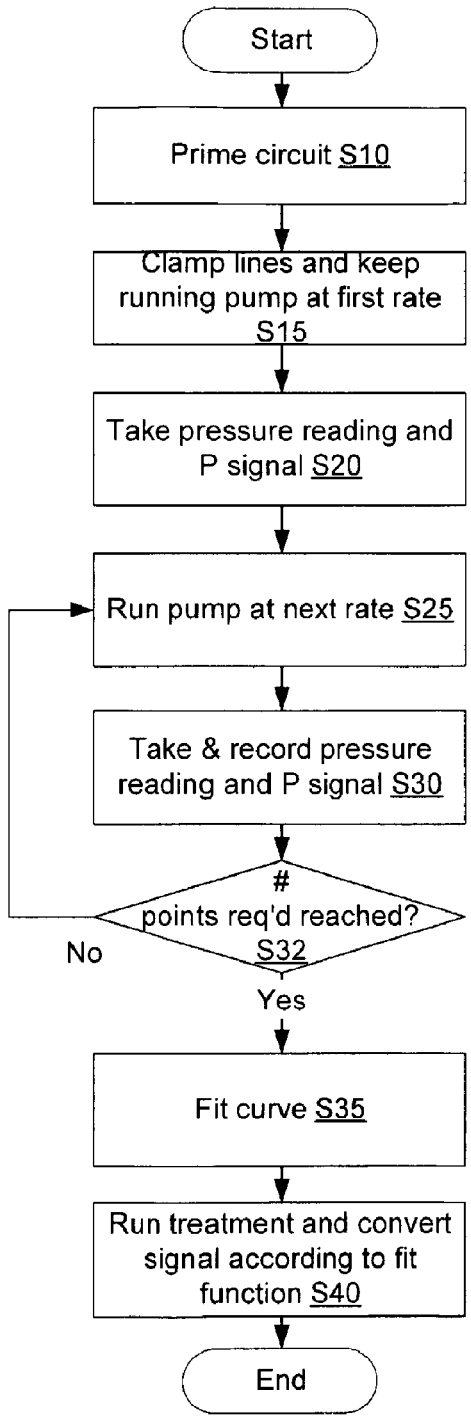
FIG. 18 is a flow chart showing a method for implementing a pressure transducer to make measurements according to one or more aspects of the present invention.

FIG. 18 provides a flowchart that illustrates a procedure for standardizing the pressure sensor described above. The circuit is first primed (S10), then the lines are closed off or pinched and the pump maintains a first flow rate (S15). The controller then takes a first pressure reading from 640 of FIG. 15 and a P signal (S20) which may be a voltage signal from a pressure transducer of any of the foregoing embodiments. The pump flow rate then is changed to a second flow rate different from the first flow rate (S25), and after the system re-equilibrates the controller takes a second pressure reading and a second P signal (S30). The system then checks to determine if the required number of data points has been collected (S32). If not, steps S25, S30 and S32 are repeated until the required number of data points is collected. At that point, the data points collected are used to generate a standard curve (S35) by conventional statistical methods. When a treatment is run, the signals obtained during the run are converted to pressure values by fitting the P signals to the standard curve (S40).

Note that in any of the foregoing embodiments, it is possible to provide for some preload of the vessel/tube or support thereof such that when there is a negative pressure in the vessel/tube, it does not collapse. Under such circumstances, any of the above embodiments may allow for the measurement of negative gage pressures in the same manner as positive gage pressure is measured. Certain kinds of vessels/tubes would not provide a substantial preload without an external support, however, for example thin-walled vessels/tubes or those with walls with large area relative to thickness.

Figure 19A:
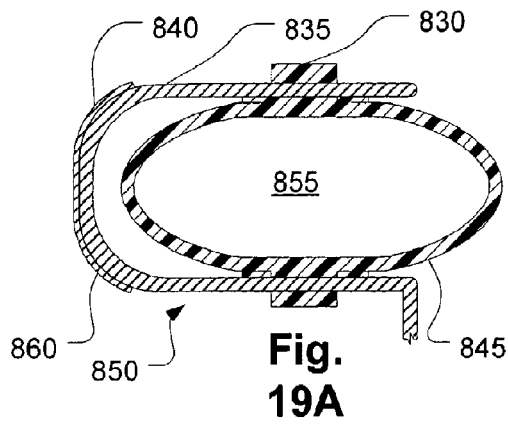
FIGS. 19A and 19B illustrate certain principles and design features that may be provided to ensure that pressures of fluids at negative gage pressures can be measured.
Figure 19B:
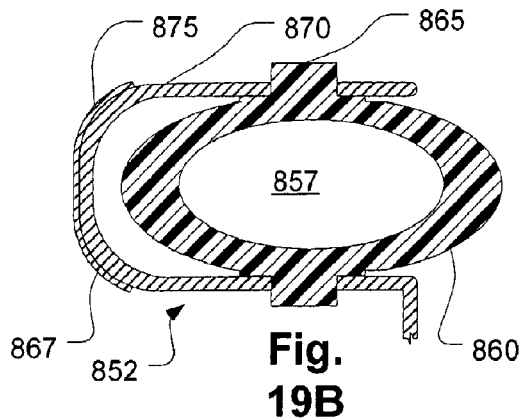

Referring to FIG. 19A, a vessel or tube 845 has molded portions 830 that engage with arms 835 of a spring 850. The spring 850 has attached to a base portion 860 thereof, a strain sensor 840 to detect changes in shape of the spring 850. The engagement between the spring 850 and molded portions 830 is such that if a negative pressure develops within an interior 855 of the vessel or tube 845, the tendency of the vessel or tube 845 to collapse may be resisted by the spring 850. In the configuration of FIG. 19A, it may be that the resilience of the spring 850 ensures against collapse of the vessel or tube 845 if the vessel or tube 845 lacks sufficient integrity to avoid collapse with the help of the spring 850. In such a case the spring 850 would relax when there is zero gage pressure in the interior 855 and would experience reverse tension when the interior pressure dropped below gage pressure. But the same result may be achieved even if the spring were always under tension in the same direction as positive if the structure of the vessel or tube is such that a positive preloading is presented to the spring. Referring to FIG. 19B, a thick-walled vessel or tube 860 is squeezed by a spring 870, the force of the spring being resisted by the vessel or tube 860 even when its interior 857 is under negative pressure. Thus, it should be clear that the pressure sensors of at least some of the earlier embodiments may be altered as illustrated by the examples of FIGS. 19A and 19B to provide for measurement of negative pressure. Note that another alternative to provide for positive loading when the vessel or tube is under negative pressure is a third spring, for example, one mounted inside the vessel or tube.

It will be evident to those skilled in the art that the invention is not limited to the details of the foregoing illustrative embodiments, and that the present invention may be embodied in other specific forms without departing from the spirit or essential attributes thereof. For example, although load cells and strain gages are disclosed as a preferred mechanism for detecting shape change of fluid vessels or tubes, it is possible to detect such shape change by other means. For example, any kind of displacement transducer such as a mechanical, resistance, or optical encoder could be used to measure the change in shape of the tube or vessel due to pressure variation. In fact, even non-contact detectors could be used, for example, an interferometric displacement encoder.

The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A pressure measurement device, comprising:
   a fluid circuit for conducting a fluid in support of renal replacement therapy;
   said fluid circuit having a tubular part with a sensor portion;
   a mechanism adjacent said sensor portion configured to detecting pressure from said sensor portion responsive to changes in pressure of a fluid within an interior thereof;
   said sensor portion having a non-circular cross-section, at least said sensor portion being configured such that it suffers substantially no non-elastic tensile strain in a wall thereof as a result of a change in pressure within whereby hysteresis in a signal from said sensor element is avoided.

2. A device as in claim 1, wherein said mechanism includes a first support positioned to support a fixed portion of said sensor portion.

3. A device as in claim 1, wherein said mechanism includes a first support with a fixed surface positioned to support a fixed portion of said sensor portion and a displace ment sensor to detect deformation of a non-fixed portion of said sensor portion by detecting displacement thereof.

4. A device as in claim 3, wherein said displacement sensor includes a movable element with a movable surface substantially coplanar with said fixed surface.

5. A device as in claim 4, wherein said fixed and movable surfaces engage said sensor portion to preload said sensor portion such that said sensor portion remains open, whereby said non-fixed portion is displaced by changes in pressure of said interior in a negative range of gage pressures.

6. A device as in claim 5, wherein a load generated by preloading is borne at least in part by a spring.

7. A device as in claim 1, wherein said sensor portion is a flattened portion of said tubular part.

8. A device as in claim 7, wherein said mechanism includes a first support positioned to support a fixed portion of said sensor portion.

9. A device as in claim 7, wherein said mechanism includes a first support with a fixed surface positioned to support a fixed portion of said sensor portion and a displacement sensor to detect deformation of a non-fixed portion of said sensor portion by detecting displacement thereof.

10. A device as in claim 9, wherein said displacement sensor includes a movable element with a movable surface substantially coplanar with said fixed surface.

* * * * *